United States Patent
Kudo (10) Patent No.: US 10,817,753 B2
(45) Date of Patent: *Oct. 27, 2020

(54) LEARNING ASSISTANCE DEVICE, METHOD OF OPERATING LEARNING ASSISTANCE DEVICE, LEARNING ASSISTANCE PROGRAM, LEARNING ASSISTANCE SYSTEM, AND TERMINAL DEVICE

(71) Applicant: FUJIFILM Corporation, Tokyo (JP)

(72) Inventor: Yuya Kudo, Tokyo (JP)

(73) Assignee: FUJIFILM Corporation, Tokyo (JP)

(*) Notice: Subject to any disclaimer, the term of this patent is extended or adjusted under 35 U.S.C. 154(b) by 23 days.

This patent is subject to a terminal disclaimer.

(21) Appl. No.: 16/129,923

(22) Filed: Sep. 13, 2018

(65) Prior Publication Data

US 2019/0095760 A1 Mar. 28, 2019

(30) Foreign Application Priority Data

Sep. 27, 2017 (JP) .................................. 2017-187095

(51) Int. Cl.
| | |
|---|---|
| *G06K 9/62* | (2006.01) |
| *G16H 30/20* | (2018.01) |
| *G16H 10/60* | (2018.01) |
| *G16H 40/20* | (2018.01) |
| *G16H 30/40* | (2018.01) |
| *G16H 50/70* | (2018.01) |
| *G06K 9/00* | (2006.01) |

(52) U.S. Cl.
CPC ....... *G06K 9/6262* (2013.01); *G06K 9/00979* (2013.01); *G06K 9/627* (2013.01); *G06K 9/6227* (2013.01); *G06K 9/6256* (2013.01); *G16H 10/60* (2018.01); *G16H 30/20* (2018.01); *G16H 30/40* (2018.01); *G16H 40/20* (2018.01); *G16H 50/70* (2018.01); *G06K 2209/05* (2013.01)

(58) Field of Classification Search
CPC ............ G06K 9/6227; G06K 9/00979; G06K 9/6262; G06K 9/627; G06K 2209/05; G16H 40/20; G16H 10/60; G16H 30/40; G16H 50/70; G16H 30/20
USPC ........................................................ 382/159
See application file for complete search history.

(56) References Cited

U.S. PATENT DOCUMENTS

2007/0217688 A1* 9/2007 Sabe .................. G06K 9/00228
382/226

FOREIGN PATENT DOCUMENTS

JP 2008-46729 A 2/2008

* cited by examiner

*Primary Examiner* — Huy C Ho
(74) *Attorney, Agent, or Firm* — Birch, Stewart, Kolasch & Birch, LLP (57) ABSTRACT

The learning assistance device acquires a plurality of learned discriminators obtained by causing learning discriminators provided in a plurality of respective terminal devices to perform learning using image correct answer data, sets the learned discriminator having the highest correct answer rate among the plurality of learned discriminators as a new learning discriminator, and outputs the learning discriminator and identification information capable of identifying the image correct answer data used for learning. The plurality of terminal devices repeatedly performs a process of outputting a plurality of learned discriminators obtained by causing the learning discriminators to perform learning using image correct answer data different from image correct answer data indicated by the identification information.

16 Claims, 6 Drawing Sheets

LEARNING ASSISTANCE DEVICE, METHOD OF OPERATING LEARNING ASSISTANCE DEVICE, LEARNING ASSISTANCE PROGRAM, LEARNING ASSISTANCE SYSTEM, AND TERMINAL DEVICE

CROSS-REFERENCE TO RELATED APPLICATION

This application claims priority from Japanese Patent Application No. 2017-187095, filed on Sep. 27, 2017, the disclosure of which is incorporated by reference herein in its entirety.

BACKGROUND

Field of the Invention

The present invention relates to a learning assistance device that assists in generation of a discriminator using machine learning, a method of operating the learning assistance device, a learning assistance program, a learning assistance system, and a terminal device.

Related Art

In the related art, machine learning has been used to learn features of data and perform recognition or classification of images or the like. In recent years, various learning schemes have been developed, a processing time has been shortened due to an improved processing capability of a computer, and deep learning in which a system learns features of image data or the like at a deeper level can be performed. By performing deep learning, features of images or the like can be recognized with very high accuracy, and improvement of performance of discrimination is expected.

In the medical field, artificial intelligence (AI) that recognizes features of images with high accuracy by performing learning using deep learning is desired. For deep learning, it is indispensable to perform learning using a large amount of high-quality data according to purposes. Therefore, it is important to prepare learning data efficiently. Image data of a large number of cases of disease is accumulated in each medical institution with the spread of a picture archiving and communication system (PACS). Therefore, learning using image data of various cases of disease accumulated in each medical institution is considered.

Further, in recent years, a technical level of artificial intelligence has been improving in a variety of fields, and artificial intelligence is incorporated into a variety of services and started to be used and utilized. In particular, services provided to various edge terminals over a network are increasing. For example, JP2008-046729A discloses a device in which a learning model is incorporated into a moving image topic division device that automatically divides a moving image at a switching point of a topic. JP2008-046729A discloses that the learning model has been distributed to a client terminal, the topic division is automatically executed using the distributed learning model at each client terminal, and content corrected by a user for a result of the automatic topic division is fed back for updating of the learning model. After the feedback corrected by the user is accumulated in an integration module over a network, a learning model reconstructed using the accumulated feedback is distributed to each client terminal over the network again.

However, in the medical field, since data to be learned is medical data of a patient, confidentiality is very high, and it is necessary to handle data carefully for use as learning data. Therefore, it is difficult and costly to collect learning data efficiently. Further, since quality of artificial intelligence applied to the medical field is required to be kept constant, a mechanism for evaluating a certain level being reached after learning is required.

SUMMARY

Therefore, in order to solve the above-described problems, an object of the present invention is to provide a learning assistance device which enables learning of a large amount and a variety of learning data necessary for deep learning in a medical field, a method of operating the learning assistance device, a learning assistance program, a learning assistance system, and a terminal device.

A learning assistance device of the present invention comprises a learned discriminator acquisition unit that acquires a plurality of learned discriminators obtained by causing learning discriminators provided in a plurality of respective terminal devices to perform learning using image correct answer data; and a discriminator output unit that obtains a correct answer rate using an image set including a plurality of images for the plurality of learned discriminators, sets the learned discriminator having the highest correct answer rate among the plurality of learned discriminators as a new learning discriminator, and outputs the new learning discriminator and identification information capable of identifying the image correct answer data used for learning of the new learning discriminator, wherein the learning assistance device repeatedly performs a process in which the learned discriminator acquisition unit acquires the plurality of learned discriminators obtained by causing the learning discriminators output from the discriminator output units and provided in the plurality of respective terminal devices to perform learning using image correct answer data different from image correct answer data indicated by the output identification information, and the discriminator output unit outputs the new learning discriminator and the identification information of the image correct answer data learned by the new learning discriminator.

A method of operating a learning assistance device of the present invention is a method of operating a learning assistance device including a learned discriminator acquisition unit and a discriminator output unit, the method comprising: acquiring a plurality of learned discriminators obtained by causing learning discriminators provided in a plurality of respective terminal devices to perform learning using image correct answer data by the learned discriminator acquisition unit; obtaining a correct answer rate using an image set including a plurality of images for the plurality of learned discriminators, setting the learned discriminator having the highest correct answer rate among the plurality of learned discriminators as a new learning discriminator, and outputting the new learning discriminator and identification information capable of identifying the image correct answer data used for learning of the new learning discriminator by the discriminator output unit; and repeatedly performing a process in which the learned discriminator acquisition unit acquires the plurality of learned discriminators obtained by causing the learning discriminators output from the discriminator output units and provided in the plurality of respective terminal devices to perform learning using image correct answer data different from image correct answer data indicated by the output identification information, and the discriminator output unit outputs the new learning discriminator and the identification information of the image correct answer data learned by the learning discriminator.

A learning assistance program of the present invention causes a computer to function as: a learned discriminator acquisition unit that acquires a plurality of learned discriminators obtained by causing learning discriminators provided in a plurality of respective terminal devices to perform learning using image correct answer data; and a discriminator output unit that obtains a correct answer rate using an image set including a plurality of images for the plurality of learned discriminators, sets the learned discriminator having the highest correct answer rate among the plurality of learned discriminators as a new learning discriminator, and outputs the new learning discriminator and identification information capable of identifying the image correct answer data used for learning of the new learning discriminator, wherein the learning assistance program repeatedly performs a process in which the learned discriminator acquisition unit acquires the plurality of learned discriminators obtained by causing the learning discriminators output from the discriminator output units and provided in the plurality of respective terminal devices to perform learning using image correct answer data different from image correct answer data indicated by the output identification information, and the discriminator output unit outputs the new learning discriminator and the identification information of the image correct answer data learned by the learning discriminator.

The "image correct answer data" refers to a combination of the image data and the correct answer data of the image data. Further, the image correct answer data learned by the learning discriminator provided in the terminal device may be image correct answer data stored in the terminal device, or may be image correct answer data acquired from a device accessible by the terminal device or the storage medium.

The "identification information of image correct answer data learned by the learning discriminator" may be information capable of identifying at least image correct answer data learned immediately before the learning discriminator is acquired from a terminal device, but may be information capable of identifying all of pieces of image correct answer data learned in the past.

"Acquire a learned discriminator" may be acquiring the learned discriminator or may be receiving a parameters of the discriminator and setting the parameters in a prepared discriminator to acquire the learned discriminator. For example, in a case where the discriminator is a multilayered neural network, a program in which a learned multilayered neural network is incorporated may be acquired or weights of coupling between layers of units of the multilayered neural network may be acquired as parameters and the parameters may be set in the prepared multilayered neural network, so that the learned multilayered neural network can be acquired.

Further, the identification information output by the discriminator output unit may be identification information allowing each of the terminal devices to identify whether or not the image correct answer data learned by the learning discriminator to be output is image correct answer data learned by each of the terminal devices.

The "identification information output by the discriminator output unit" is identification information capable of identifying the image correct answer data, and "allowing to identify whether or not the image correct answer data learned by the learning discriminator to be output is image correct answer data learned by each of the terminal devices" refers to allowing each terminal device to identify whether or not the image correct answer data learned by the learning discriminator to be output is image correct answer data learned by the terminal device.

Further, it is also desirable for the discriminator output unit to output an actually operated discriminator that has learned the same image correct answer data as that of the new learning discriminator.

The "actually operated discriminator" is a discriminator capable of acquiring a discrimination result of input image data, which cannot perform additional learning, and the "learning discriminator" is a discriminator that can perform additional learning using image data constituting image correct answer data and the correct answer data.

Further, the identification information of the image correct answer data may be determined to be unique in all of the plurality of terminal devices, the learned discriminator acquisition unit may acquire identification information of the image correct answer data learned by each of the learned discriminators, and the discriminator output unit may output the identification information of the image correct answer data used for learning of the learning discriminator.

Further, the identification information of the image correct answer data may include terminal device identification information for identifying the plurality of terminal devices.

Further, the learning assistance device may further comprise an identification information distribution unit that distributes the identification information for identifying the image correct answer data to the plurality of terminal devices over a network.

Further, the learned discriminator acquisition unit may acquire the learned discriminator from the plurality of terminal devices over a network, and the discriminator output unit may output the new learning discriminator and the identification information of the image correct answer data used for learning of the learning discriminator to the plurality of terminal devices over the network.

Further, the learned discriminator acquisition unit may receive the identification information of the image correct answer data used for learning of each of the plurality of learned discriminators from each of the plurality of terminal devices over the network.

A learning assistance system according to the present invention is a learning assistance system in which a plurality of terminal devices and a learning assistance device are connected by a network, wherein the terminal device includes a learned discriminator output unit that outputs a learned discriminator obtained by causing a learning discriminator to perform learning using image correct answer data to the learning assistance device over a network, the learning assistance device includes a learned discriminator acquisition unit that acquires a plurality of learned discriminators from the plurality of respective terminal devices over the network, and a discriminator output unit that obtains a correct answer rate using an image set including a plurality of images for the plurality of learned discriminators, sets the learned discriminator having the highest correct answer rate among the plurality of learned discriminators as a new learning discriminator, and outputs the new learning discriminator and identification information capable of identifying the image correct answer data used for learning of the new learning discriminator to the plurality of terminal devices over the network, the terminal device includes a discriminator acquisition unit that acquires the learning discriminator output from the learning assistance device and identification information of image correct answer data used for learning of the acquired learning discriminator over the network, and the learned discriminator output unit outputs the learned discriminator obtained by causing the learning discriminator acquired by the discriminator acquisition unit to perform learning using image correct answer data different from the identification information used for learning of the learning discriminator acquired by the discriminator acquisition unit.

Further, the discriminator acquisition unit may further acquire an actually operated discriminator caused to learn the same image correct answer data as that of the learning discriminator output from the learning assistance device, and the terminal device may further include a discrimination result acquisition unit that acquires a discrimination result of discriminating an image that is a discrimination target using the actually operated discriminator.

A terminal device according to the present invention comprises a discriminator acquisition unit that acquires a learning discriminator, an actually operated discriminator having learned the same image correct answer data as that of the learning discriminator, and identification information capable of identifying the learned image correct answer data; a discrimination result acquisition unit that acquires a discrimination result of discriminating an image that is a discrimination target using the actually operated discriminator; and a learned discriminator output unit that outputs a learned discriminator obtained by causing the learning discriminator to learn image correct answer data different from the acquired identification information.

Further, the learned discriminator output unit may output the identification information of the different image correct answer data.

Further, the discriminator acquisition unit may acquire the learning discriminator, the actually operated discriminator, and the identification information from a learning assistance device over a network, and the learned discriminator output unit may output the learned discriminator over the network.

Another learning assistance device of the present invention comprises a memory that stores instructions to be executed by a computer, and a processor configured to execute the stored instructions, wherein the processor executes an acquisition process of acquiring a plurality of learned discriminators obtained by causing learning discriminators provided in a plurality of respective terminal devices to perform learning using image correct answer data, and an output process of obtaining a correct answer rate using an image set including a plurality of images for the plurality of learned discriminators, setting the learned discriminator having the highest correct answer rate among the plurality of learned discriminators as a new learning discriminator, and outputting the learning discriminator and identification information capable of identifying the image correct answer data used for learning of the learning discriminator, and wherein a process in which the plurality of learned discriminators obtained by causing the learning discriminators provided in the plurality of respective terminal devices and output from the discriminator output units to perform learning using image correct answer data different from image correct answer data indicated by the output identification information is acquired through the acquisition process, and the new learning discriminator and the identification information of the image correct answer data learned by the learning discriminator are output through the output process is repeatedly executed.

According to the present invention, the learning assistance device acquires the plurality of learned discriminators obtained by causing learning discriminators provided in a plurality of respective terminal devices to perform learning using image correct answer data, obtains the correct answer rate using the image set including a plurality of images for the plurality of learned discriminators, sets the learned discriminator having the highest correct answer rate among the plurality of learned discriminators as a new learning discriminator, outputs the learning discriminator and the identification information capable of identifying the image correct answer data used for learning, and transfers the learning discriminator and the identification information to the terminal device, which is repeatedly performed. Thus, it is possible to improve discrimination performance of the discriminator using a large amount of image correct answer data in a facility in which a plurality of terminal devices are placed. Further, since the image data in each terminal device is not distributed to the outside, it is possible to perform deep learning using a large number of images even for images with high confidentiality such as medical images, and to improve performance of the discrimination.

DETAILED DESCRIPTION

Figure 1:
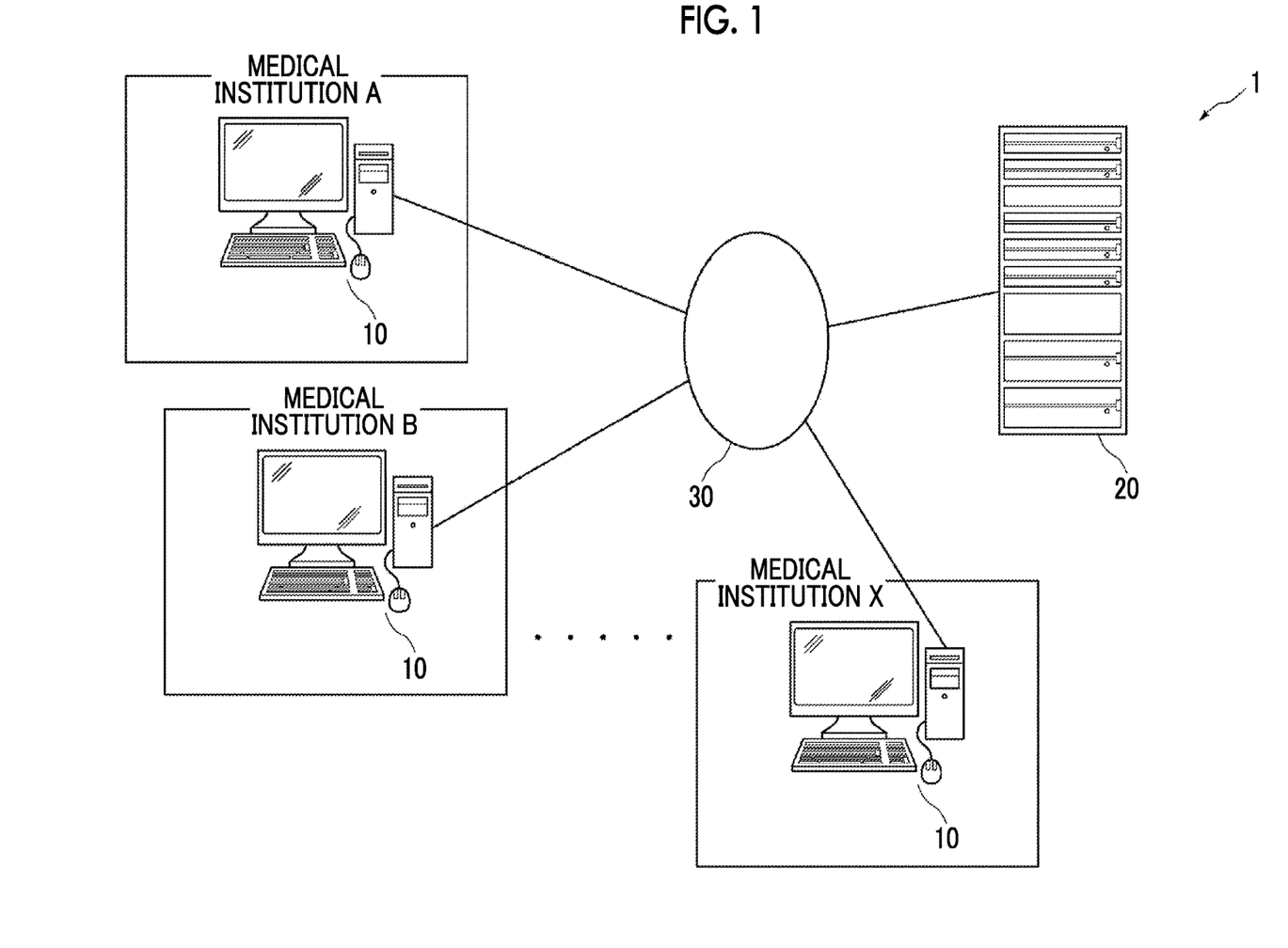
FIG. 1 is a diagram illustrating a schematic configuration of a learning assistance system of the present invention.

FIG. 1 illustrates a schematic configuration of a learning assistance system 1 according to an embodiment of the present invention. The learning assistance system 1 is configured by connecting a plurality of terminal devices 10 installed in a plurality of medical institutions A, B, . . . , X and a learning assistance device 20 placed on a cloud side over a network 30.

The learning assistance device 20 includes a well-known hardware configuration such as a central processing unit (CPU), a memory, a storage, an input and output interface, a communication interface, an input device, a display device, and a data bus, and is a high-performance computer in which a well-known operation system or the like is installed and which has a server function. Further, a graphics processing unit (GPU) may be provided, as necessary. Alternatively, the learning assistance device 20 may be a virtualized virtual server provided using one or a plurality of computers. The learning assistance program of the present invention is installed in a server, and functions as a learning assistance device by a program instruction being executed by the CPU of the computer.

The terminal device 10 is a computer for image processing provided in the respective medical institutions A, B, . . . , X, and includes a well-known hardware configuration such as a CPU, a memory, a storage, an input and output interface, a communication interface, an input device, a display device, and a data bus. A well-known operation system or the like is installed in the terminal device 10. The terminal device 10 includes a display as a display device. Further, a GUP may be provided, as necessary.

The network 30 is a wide area network (WAN) that widely connects the terminal devices 10 placed at the plurality of medical institutions A, B, . . . , X to the learning assistance device 20 via a public network or a private network.

Figure 2:
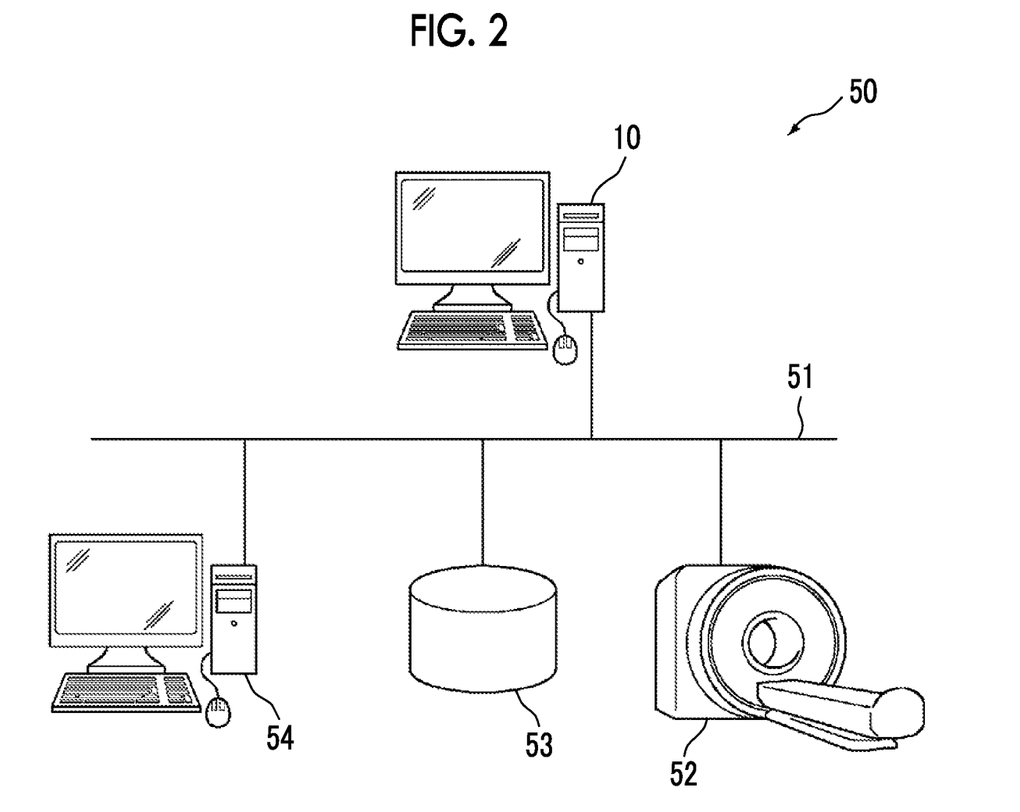
FIG. 2 is a diagram illustrating a schematic configuration of a medical information system.

Further, as illustrated in FIG. 2, the terminal device 10 is connected to a medical information system 50 of the respective medical institutions A, B, . . . , X over a local area network (LAN) 51. The medical information system 50 includes a modality (an imaging device) 52, an image database 53, and an image interpretation medical workstation 54, and is configured so that transmission and reception of image data to and from each other are performed over the network 51. It should be noted that in the network 51, it is desirable to use a communication cable such as an optical fiber so that image data can be transferred at a high speed.

The modality 52 includes a device that images an examination target part of a subject to generate an examination image representing the part, adds accessory information defined in a DICOM standard to the image, and outputs the resultant image. Specific examples of the device include a computed tomography (CT) device, a magnetic resonance imaging (MRI) device, a positron emission tomography (PET) device, an ultrasonic device, and a computed radiography (CR) device using a planar X-ray detector (FPD: flat panel detector).

In the image database 53, a software program for providing a function of a database management system (DBMS) is incorporated in a general-purpose computer, and a large capacity storage is included. This storage may be a large capacity hard disk device, or may be a disk device connected to a network attached storage (NAS) or a storage area network (SAN) connected to the network 51. Further, the image data captured by the modality 52 is transmitted to and stored in the image database 53 over the network 51 according to a storage format and a communication standard conforming to a DICOM standard.

The image interpretation medical workstation 54 is a computer that is used for an image interpretation doctor of a radiology department to interpret an image and create an interpretation report. The image interpretation medical workstation 54 performs a display of the image data received from the image database 53 and performs automatic detection of a portion likely to be a lesion in the image.

In the embodiment, a case where an image processing program in which a discriminator functioning as an actually operated discriminator is incorporated in each terminal device 10 is provided from the learning assistance device 20, and a learning program in which a discriminator functioning as a learning program separately from the image processing program is incorporated is provided will be described. The image processing program and the learning program distributed to each terminal device 10 are installed in the terminal device 10 to function as an image processing device in which the actually operated discriminator is incorporated, and a learning discriminator.

Further, a case where the actually operated discriminator and the learning discriminator are multilayered neural networks subjected to deep learning to be able to discriminate a plurality of types of organ areas and/or lesion areas will be described. In the multilayered neural network, a calculation process is performed on a plurality of pieces of different calculation result data obtained by a preceding layer for input data, that is, extraction result data of a feature amount using various kernels in each layer, data of the feature amount obtained by the calculation process is acquired, and a further calculation process is performed on the data of the feature amount in the next and subsequent processing layers. Thus, it is possible to improve a recognition rate of the feature amount and to discriminate which of a plurality of types of areas the input image data is.

Figure 3:
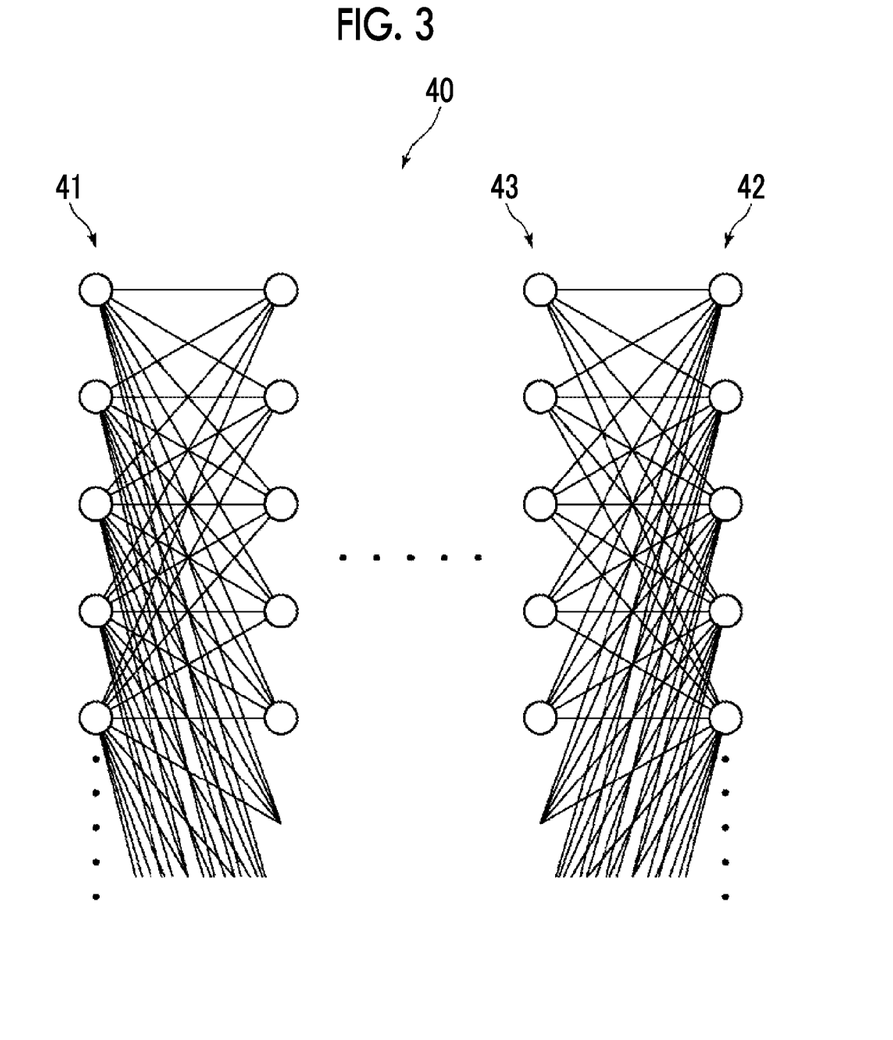
FIG. 3 illustrates an example of a multilayered neural network.

FIG. 3 is a diagram illustrating an example of the multilayered neural network. As illustrated in FIG. 3, the multilayered neural network 40 includes a plurality of layers including an input layer 41 and an output layer 42. In FIG. 3, a layer before the output layer 42 is denoted by reference numeral 43.

In the multilayered neural network 40, the image data is input to the input layer 41 and a discrimination result of an area is output. In a case where learning is performed, the output discrimination result is compared with correct answer data, and weights of coupling between the respective layers of units (indicated by circles in FIG. 3) included in the respective layers of the multilayered neural network 40 is corrected from the output side (the output layer 42) to the input side (the input layer 41) according to whether an answer is a correct answer or an incorrect answer. The correction of the weights of coupling is repeatedly performed a predetermined number of times, or is repeatedly performed until a correct answer rate of the output discrimination result is 100% or is equal to or greater than a predetermined threshold value using a large number of pieces of image data with correct answer data, and the learning ends.

Figure 4:
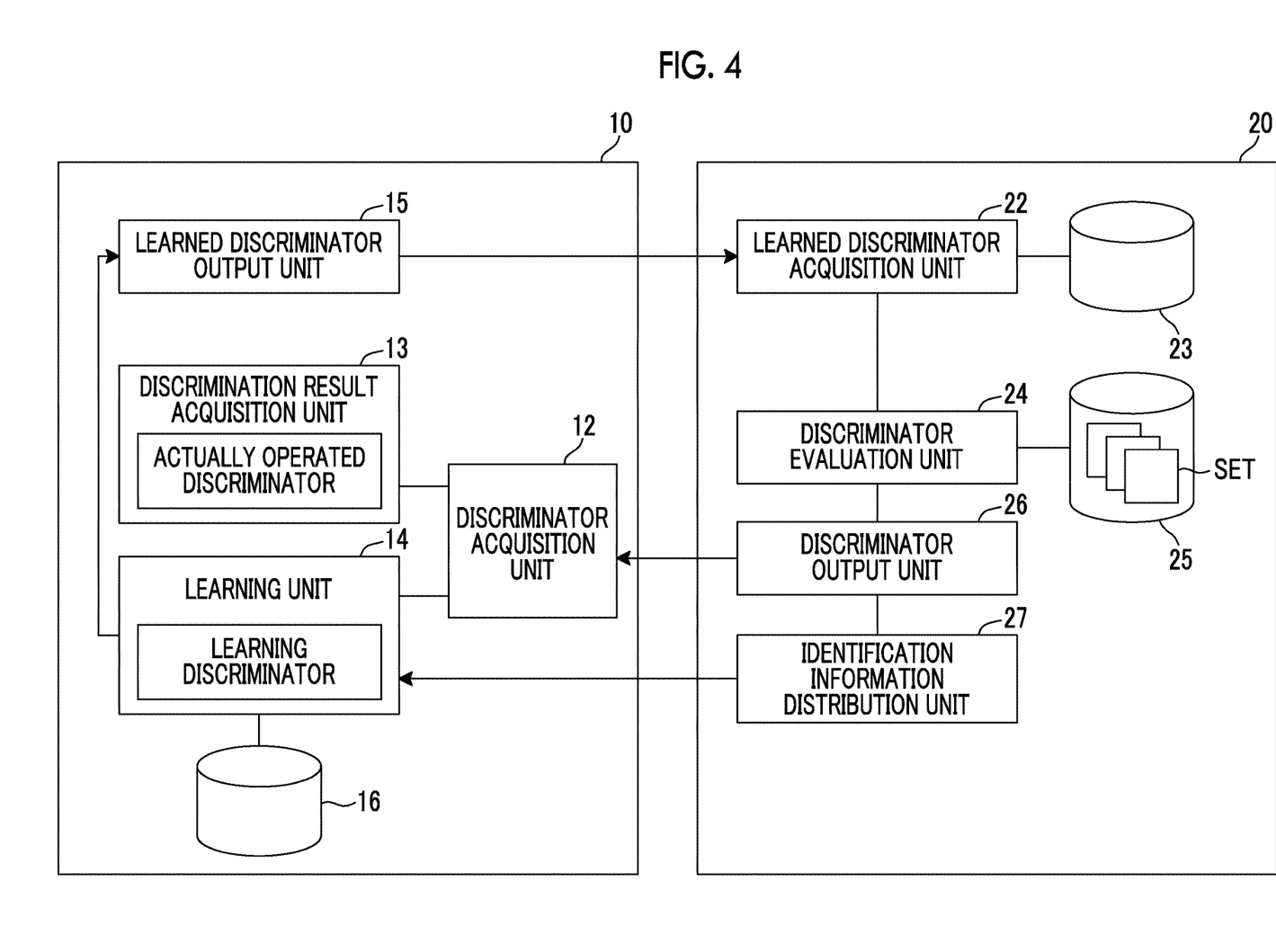
FIG. 4 is a block diagram illustrating a schematic configuration of a terminal device and a learning assistance device.

FIG. 4 is a block diagram illustrating a schematic configuration of the terminal device 10 and the learning assistance device 20. Functions of the terminal device 10 and the learning assistance device 20 will be described in detail with reference to FIG. 4. First, the terminal device 10 will be described.

The terminal device 10 includes a discriminator acquisition unit 12, a discrimination result acquisition unit 13, a learning unit 14, a learned discriminator output unit 15, and a correct answer image storage unit 16.

The discriminator acquisition unit 12 acquires a learning discriminator and an actually operated discriminator. For example, the image processing program and the learning program are received from the learning assistance device 20 over the network 30, and the received image processing program is installed. Accordingly, image processing in which the actually operated discriminator is incorporated becomes executable in the terminal device 10 and functions as the discrimination result acquisition unit 13. At the same time, the learning program is installed, and the learning discriminator becomes executable and functions as the learning unit 14. It should be noted that the learning discriminator is a discriminator that has learned the same image correct answer data as the actually operated discriminator received from the learning assistance device 20. In the following description, the image processing in which the actually operated discriminator is incorporated is simply referred to as an actually operated discriminator.

Further, the discriminator acquisition unit 12 receives an identification information ID capable of identifying the image correct answer data used for learning by the learning discriminator. It should be noted that the image correct answer data refers to a combination of the image data and correct answer data thereof. Details of the image correct answer data will be described below.

The discrimination result acquisition unit 13 inputs a discrimination target image to the actually operated discriminator and acquires a discrimination result. The actually operated discriminator is a discriminator of which discrimination performance has been guaranteed in the learning assistance device 20, and in each of the medical institutions A, B, ..., X, the discrimination is performed on the image data that is a diagnosis target using the actually operated discriminator. Further, the discrimination result acquisition unit 13 may perform discrimination of the image data that is a diagnosis target sent from the image interpretation medical workstation 54 to the terminal device 10 over the network 51, and transmit a discrimination result from the terminal device 10 to the image interpretation medical workstation 54.

The learning unit 14 causes the learning discriminator to perform learning using the image data and the correct answer data thereof. The correct answer data includes a mask image showing an area such as an organ or abnormal shadow of the image data, and information indicating what the area of the mask image is (for example, an area of an organ such as a liver, a kidney, or a lung or an area of an abnormal shadow such as a liver cancer, a kidney cancer, or a pulmonary nodule).

The correct answer data may be created by an image interpretation doctor or the like of each of the medical institutions A, B, ..., X observing the image data. For example, the image data is extracted from the image database 53, the discrimination result acquisition unit 13 inputs the image data to the actually operated discriminator and acquires a discrimination result, and a user such as the image interpretation doctor determines whether the discrimination result is a correct answer or an incorrect answer, and stores a discrimination result together with the input image data and correct answer data in the image database 53 as image correct answer data in the case of the correct answer. In the case of an incorrect answer, the user generates a mask image of the correct answer data, assigns the correct answer data to the image data, and stores the resultant data in the image database 53 as image correct answer data.

Therefore, the learning unit 14 causes the multilayered neural network 40 of the learning discriminator to perform learning using a large number of pieces of image correct answer data stored in the image database 53. First, the image data of the image correct answer data is input to the multilayered neural network 40, and a discrimination result is output. Then, the output discrimination result is compared with the correct answer data, and weights of coupling between the respective layers of the units included in the respective layers of the multilayered neural network 40 from the output side to the input side is corrected according to whether the answer is a correct answer or an incorrect answer. The correction of the weights of the coupling is repeatedly performed using a large number of correct answer data a predetermined number of times or until the correct answer rate of the output discrimination result becomes 100%, and the learning is ended.

It should be noted that the learning unit 14 performs learning using image correct answer data different from the image correct answer data indicated by the identification information ID received by the discriminator acquisition unit 12. Further, the learning unit 14 assigns a new identification information ID issued from the learning assistance device 20 to the learned image correct answer data, and stores the learned image correct answer data in the storage (correct answer image storage unit) 16 so that the learned image correct answer data can be used in a case where re-learning is required.

The learned discriminator output unit 15 outputs the learning discriminator of which the learning has ended in the learning unit 14 as a learned discriminator. Specifically, the weights (hereinafter referred to as parameters) of coupling between the layers of the units constituting the neural network constituting the learned discriminator and the identification information ID of the image correct answer data learned by the learned discriminator are periodically transmitted to the learning assistance device 20 over the network 30.

Next, the learning assistance device 20 will be described. As illustrated in FIG. 4, the learning assistance device 20 includes a learned discriminator acquisition unit 22, a discriminator storage unit 23, a discriminator evaluation unit 24, an evaluation image storage unit 25, a discriminator output unit 26, and an identification information distribution unit 27.

The learned discriminator acquisition unit 22 receives parameters of the multilayered neural network 40 constituting the learned discriminators transmitted from the plurality of terminal devices 10 over the network 30. The received parameters are temporarily stored in the discriminator storage unit 23. The multilayered neural network 40 is provided in the learning assistance device 20 in advance and the parameters received from each terminal device 10 is set as the weights of the coupling between the respective layers of the units of the multilayered neural network 40 provided in the learning assistance device 20. By re-setting the parameters received from each terminal device in these weights, the same learned discriminator as each terminal device 10 can be acquired. Further, each terminal device 10 receives the identification information ID of the learned image correct answer data together with the parameters.

The discriminator evaluation unit 24 evaluates the learned discriminator collected from each terminal device 10 using the evaluation image set including the evaluation image and the correct answer data of the image to obtain a correct answer rate. Specifically, the parameters received from each terminal device 10 is evaluated with respect to a discriminator set in the multilayered neural network 40 using an image set for evaluation, and the respective correct answer rates of the learned discriminators learned in the respective terminal devices 10 are acquired. Since software intended for medical purposes is a target of the Pharmaceutical and Medical Device Act (the revised Pharmaceutical Affairs Act), the software is required to meet a criterion prescribed in the Pharmaceutical and Medical Device Act. Therefore, an evaluation image set SET formed through a combination of a plurality of images in which the criterion prescribed in the Pharmaceutical and Medical Device Act can be evaluated is previously stored in the evaluation image storage unit 25.

Further, it is necessary for the discriminator to be a discriminator of which the correct answer rate for the evaluation image set SET exceeds a predetermined criterion so as to satisfy the criterion prescribed in the Pharmaceutical and Medical Device Act, such that the discriminator is adopted as an actually operated discriminator. Therefore, the discriminator output unit 26 sets the learned discriminator having the highest correct answer rate among the learned discriminators of which the correct answer rate exceeds the predetermined criterion as a new learning discriminator, and periodically distributes the learning discriminator and the identification information ID of the image correct answer data used for learning of the learning discriminator to the terminal device 10 of each medical institution over the network. Further, the discriminator output unit 26 distributes the actually operated discriminator learned using the same image correct answer data as the learning discriminator together with the learning discriminator.

The identification information distribution unit 27 issues the identification information ID assigned to the image correct answer data caused to be learned by each terminal device 10 and distributes the identification information ID to each terminal device 10. As each identification information ID of each image correct answer data, an identification information ID unique across all the medical institutions is assigned so that it can be discriminated whether or not image correct answer data is image correct answer data that has already been learned. The identification information ID may be distributed to each terminal device 10 together with the learning discriminator over a network, or each time the learning discriminator is caused to learn the image correct answer data in each terminal device 10, the learning unit 14 may request to issue the identification information ID over the network so that the identification information ID is issued and distributed according to a request from each terminal device 10.

In the respective medical institutions A, B, ..., X, in a case where the discriminator is caused to learn the image correct answer data accumulated in the medical information system 50 in the medical institutions, it is possible to learn more pieces of image correct answer data. However, in a case where learning is performed in the terminal device 10 of the medical institution A, the correct answer rate increases for the image data similar to the newly learned image correct answer data a, but the correct answer rate may decrease for image data b of a different type from the image correct answer data a. For actual use for diagnosis, a discriminator having a correct answer rate exceeding a predetermined criterion is required for various types of image data. Therefore, the discrimination result acquisition unit 13 of the terminal device 10 obtains the discrimination result using the actually operated discriminator of which discrimination performance has been guaranteed in the learning assistance device 20.

Next, a flow of a deep learning process of the embodiment will be described with reference to a transition diagram of FIG. 5 and a flowchart of FIG. 6.

First, in the learning assistance device 20, the discriminator output unit 26 distributes an actually operated discriminator NNo and a learning discriminator NNt to the plurality of terminal devices 10 over the network 30 (S1). Further, the identification information distribution unit 27 issues and distributes the identification information ID to be assigned to the image correct answer data, together with the distribution of these discriminators (S2). In the example of FIG. 5, ID (aaa0) is distributed to the medical institution A, ..., ID (xxx0) is distributed to the medical institution X. Although there are a plurality of medical institutions other than the medical institution A and the medical institution X, the medical institution A and the medical institution X will be described by way of example.

In the terminal device 10, the discriminator acquisition unit 12 acquires the actually operated discriminator NNo and the learning discriminator NNt (S3). In the medical institution A and the medical institution X, the actually operated discriminator NNo is used for diagnosis by the image interpretation doctor, and a discrimination result (an output) of discriminating the image data (an input) that is a diagnosis target is obtained by the discrimination result acquisition unit 13. Further, in the medical institution A, the learning unit 14 of the terminal device 10 causes the learning discriminator NNt to perform learning using the image correct answer data T already stored in the image database 53 (S4), and generates the learned discriminator NNt-A (S5). The identification information ID (aaa0) is assigned to the image correct answer data used for learning, which is stored in the storage 16a (S6). Similarly, in the medical institution X, the learning unit 14 of the terminal device 10 causes the learning discriminator NNt to perform learning using the image correct answer data T to generate a learned discriminator NNt-X (S5). The identification information ID (xxx0) is assigned to the image correct answer data used for learning, which is stored in the storage 16x (S6).

Figure 5:
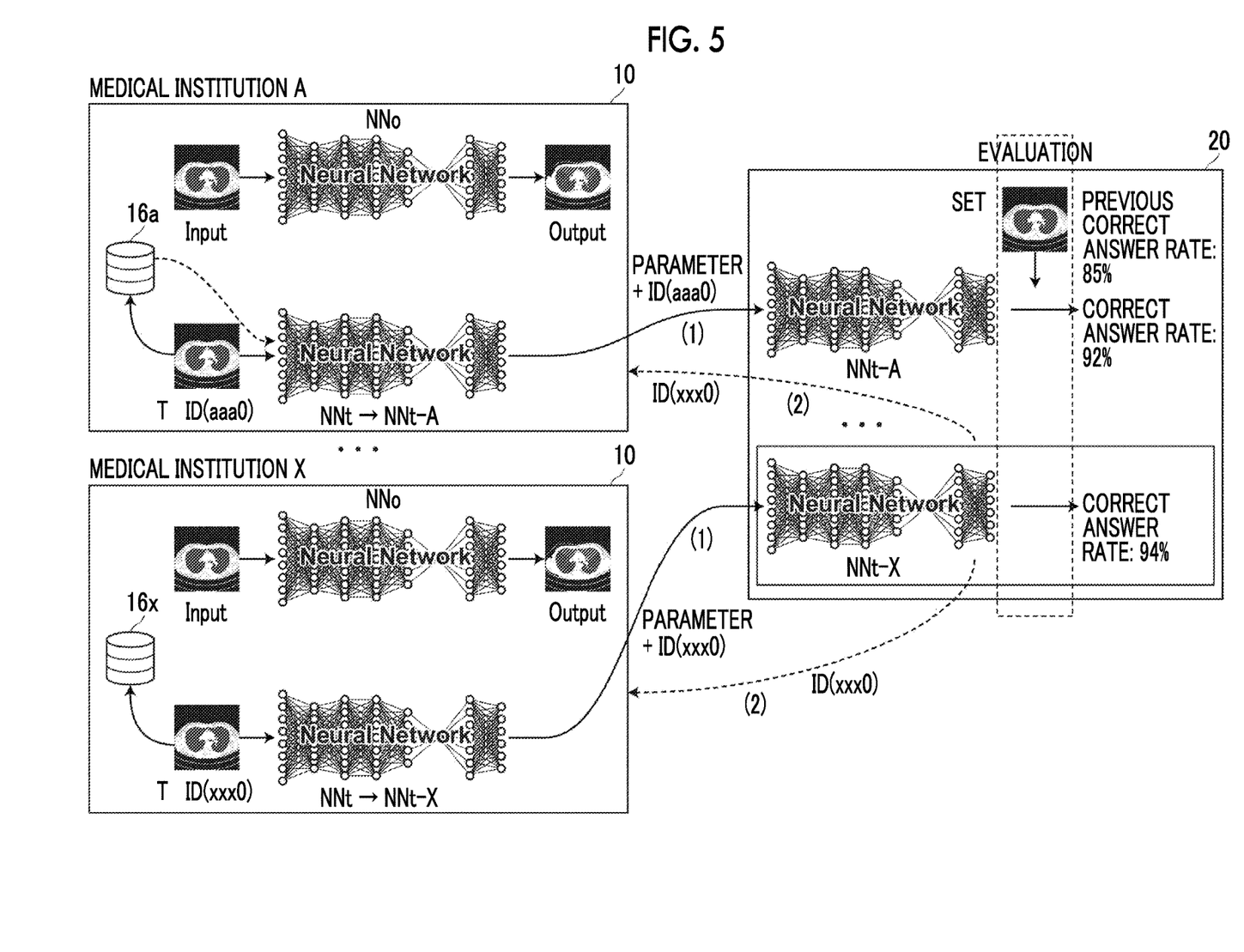
FIG. 5 is a diagram illustrating learning of a discriminator.
Figure 6:
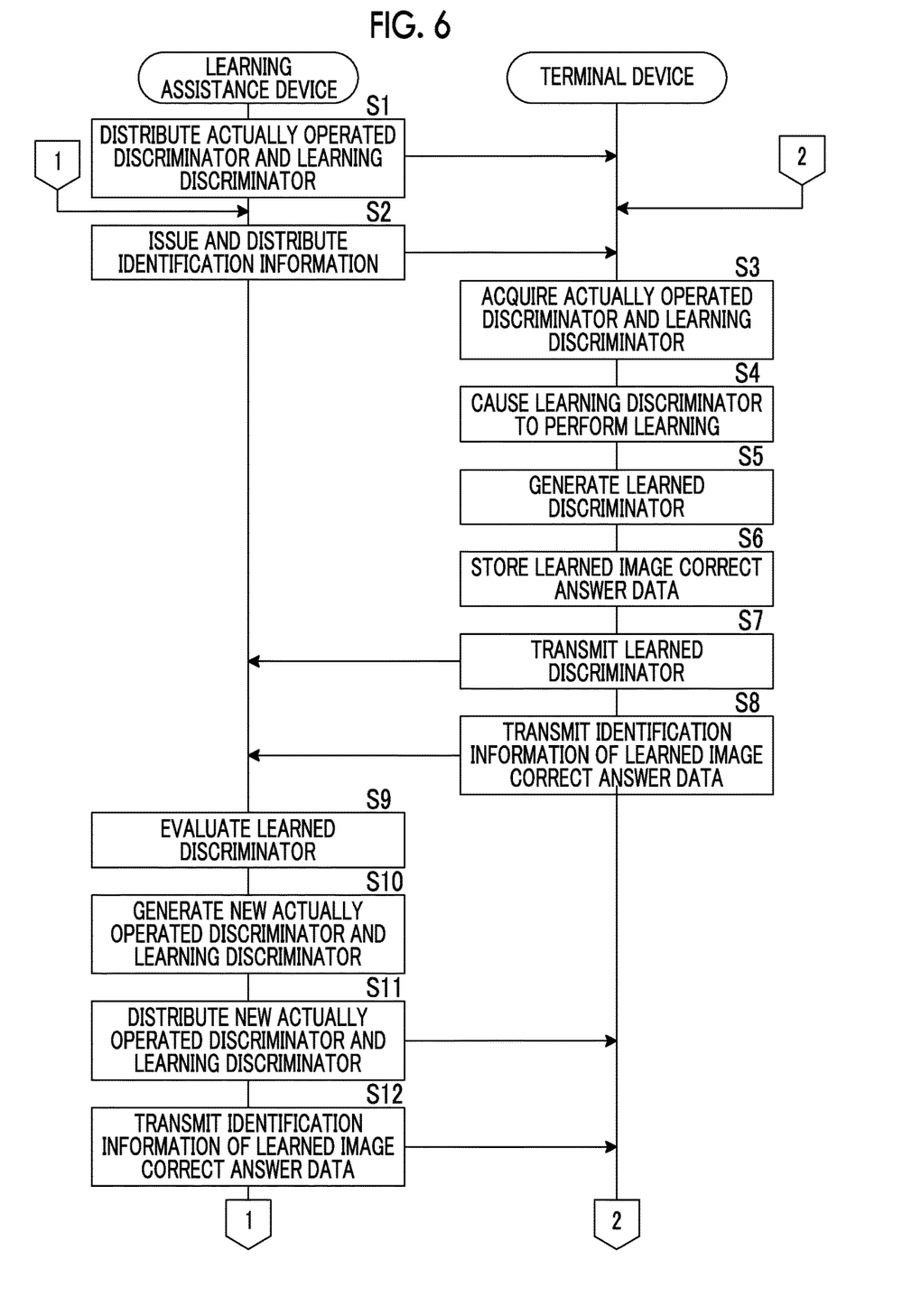
FIG. 6 is a flowchart showing a flow of a process of causing the discriminator to perform learning.

Periodically, in each terminal device 10 of the respective medical institutions A and X, the learned discriminator output unit 15 transmits the learned discriminator to the learning assistance device 20 (S7) and transmits identification information ID of the image correct answer data T used for learning to the learning assistance device 20 (S8; see a solid arrow of (1) in FIG. 5). The parameters of the learned discriminator NNt-A and the identification information ID (aaa0) are transmitted from the terminal device 10 of the medical institution A to the learning assistance device 20 (S7), and the parameters of the learned discriminator NNt-X and the identification information ID (xxx0) are transmitted from the terminal device 10 of the medical institution X to the learning assistance device 20 (S8; see a solid arrow of (1) in FIG. 5).

In the learning assistance device 20, the learned discriminator acquisition unit 22 temporarily stores the parameters of the learned discriminators received from the plurality of terminal devices 10 in the discriminator storage unit 23. By setting these parameters in the multilayered neural network 40 provided in the learning assistance device 20, each terminal device 10 acquires the learned discriminator, and the discriminator evaluation unit 24 periodically evaluates the learned discriminator with the evaluation image set SET (S9). In the example of FIG. 5, the correct answer rate of the discriminator previously distributed to each terminal device 10 as the learning discriminator NNt is 85%. The learned discriminator NNt-A learned in the medical institution A has a correct answer rate of 92%, ..., the learned discriminator NNt-X learned in the medical institution X has a correct answer rate of 94%. In the example illustrated in FIG. 5, Since the correct answer rate of the learned discriminator NNt-X learned in the medical institution X is the highest, a new version of actually operated discriminator NNo and learning discriminator NNt are generated on the basis of the learned discriminator NNt-X (S10). The discriminator output unit 26 distributes the identification information ID (xxx0) to each terminal device 10 together with the new version of actually operated discriminator NNo and learning discriminator NNt (S11 and S12; see a dashed arrow of (2) in FIG. 5).

In the terminal device 10 of the medical institution A, the discriminator acquisition unit 12 acquires the identification information ID (xxx0) together with the new actually operated discriminator NNo and the learning discriminator NNt. Since it can be seen that the image correct answer data learned in the learning discriminator NNt is not the discriminator learned in the medical institution A from the acquired identification information ID, the image correct answer data stored in the storage 16a is used for learning again.

In the terminal device 10 of the medical institution X, the discriminator acquisition unit 12 acquires the identification information ID (xxx0) together with the new actually operated discriminator NNo and the learning discriminator NNt. Since the image correct answer data learned in the learning discriminator NNt is the discriminator learned in the medical institution X from the acquired identification information ID, learning is performed using image correct answer data different from the image correct answer data stored in the storage 16x.

As described above, by repeating the processes of S2 to S12, it is possible to learn the image data stored in various medical institutions.

As described above, by performing learning using the image data stored in the medical institution in the terminal device 10 placed in each medical institution, it is possible to use the medical images while maintaining confidentiality without providing medical images with high confidentiality to the outside, and it is possible to improve discrimination performance by learning a large number of images stored in a plurality of medical institutions.

Although the case where the unique identification information ID is distributed from the learning assistance device 20 has been described in the above description, the identification information ID for each medical institution may be allocated and managed like "ID of medical institution+serial number" for each medical institution. For example, terminal device identification information for identifying each of a plurality of terminal devices may be determined in advance, and the identification information ID may be determined through a combination of the terminal device identification information and the serial number. Even in a case where the medical institution issues the identification information ID, the identification information ID may be an ID guaranteed to be unique across all medical institutions. Thus, in a case where the identification information ID is issued by each terminal device 10, the identification information distribution unit 27 of the learning assistance device 20 may not be provided.

Alternatively, the identification information ID of the image correct answer data output by the discriminator output unit 26 may be an identification information ID capable of identifying whether or not the image correct answer data learned by the learning discriminator is the image correct answer data learned by the medical institution at each terminal device 10. For example, a combination of a version of the learning discriminator used for learning with the information of each terminal device 10 that is a transmission source of a learned discrimination device may be the identification information ID.

For example, in a case where the learned discriminator is transmitted from the terminal device 10 of medical institution A to the learning assistance device 20 after a learning discriminator of which the version is "ver 2.0" is distributed, the learning assistance device 20 sets the identification information ID of the image correct answer data learned by the received learned discriminator to "ver 2.0+A". In a case where the learning assistance device 20 adopts the learned discriminator learned by the terminal device 10 of the medical institution A as a next learning discriminator and distributes the learned discriminator as a learning discriminator of version 3.0, the discriminator output unit 26 transmits "ver 2.0+A" as the identification information ID to each terminal device 10. In a case where the identification information ID is "ver 2.0+A", it is understood that learned discriminators learned in the medical institution has not been adopted in the terminal device 10 of the medical institution X. On the other hand, the terminal device 10 of the medical institution A understands that the learned discriminator learned by the medical institution has been adopted.

Thus, the identification information may be determined so that it can be seen whether or not a newly distributed learning discriminator is a discriminator previously learned in his/her medical institution.

Further, in a case where a new learning discriminator distributed to each medical institution understands that the image correct answer data thereof has been learned in each of the medical institutions, it is possible to prevent the same image correct answer data from being repeatedly learned. On the other hand, even in a case where the image correct answer data has already been learned by the learned discriminator and the image correct answer data is not learned by the learning discriminator distributed this time, the same image correct answer data can be learned again.

Although the embodiment in which the learning assistance device 20 and the terminal device 10 are connected via the network has been described in the above description, an image processing program incorporating a discriminator functioning as an actually operated discriminator and a learning program incorporating a discriminator functioning as a learning discriminator may be stored in a recording medium such as a DVD-ROM and distributed to each medical institution, instead of over the network. Further, in a case where the learned discriminator is received from each medical institution, each terminal device 10 may store the parameters of the learned discriminator and the identification information ID of the learned image correct answer data in the recording medium and transfer the parameters and the identification information ID.

In this embodiment, the discriminator acquisition unit 12 of the terminal device 10 reads the image processing program and the learning program from the DVD-ROM to the terminal device 10 and installs the image processing program and the learning program, and reads the identification information ID of the image correct answer data used for learning of the learning discriminator from the recording medium. Further, the learned discriminator output unit 15 of the terminal device 10 records the parameters of the learned discriminator and the identification information ID of the learned image correct answer data in the DVD-ROM, and distributes the parameters and the identification information ID to an operator of the learning assistance device 20 by mailing or the like.

Further, the learned discriminator acquisition unit 22 of the learning assistance device 20 reads the parameters of the learned discriminator recorded on the DVD-ROM and the identification information ID of the learned image correct answer data. Further, the discriminator output unit 26 of the learning assistance device 20 records the image processing program, the learning program, and the identification information ID of the learned image correct answer data on the DVD-ROM and sends the DVD-ROM to an operator of the terminal device 10 by mailing or the like.

Even in a case where the learning assistance device 20 transfers the learning discriminator to the terminal device 10, the learning assistance device 20 may transfer the identification information of all of pieces of learned correct answer image data so that all of pieces of correct answer image data learned in the past can be known or may transfer only the identification information of the correct answer image data learned immediately before.

As described in detail above, in the present invention, it is possible to use a large number of medical images for deep learning without outputting medical images with high confidentiality stored in each medical institution to the outside, and to improve performance of the discrimination.

Although the case where the learning assistance device and the terminal device function on a general-purpose computer has been described above, a dedicated circuit such as an application specific integrated circuit (ASIC) or field programmable gate arrays (FPGA) that permanently stores a program for executing some of functions may be provided. Alternatively, a program instruction stored in a dedicated circuit and a program instruction executed by a general-purpose CPU programmed to use a program of a dedicated circuit may be combined. As described above, the program instructions may be executed through any combination of hardware configurations of the computer.

What is claimed is:

1. A learning assistance device, comprising a processor configured to:
acquire a plurality of learned discriminators obtained by causing learning discriminators provided in a plurality of respective terminal devices to perform learning using image correct answer data, from the respective terminal devices, each of the plurality of learned discriminators being learned at the respective terminal devices by using respective image correct answer data stored in the respective terminal devices; and
obtain a correct answer rate using an image set including a plurality of evaluation images for the plurality of learned discriminators, set the learned discriminator having the highest correct answer rate among the plurality of learned discriminators as a new learning discriminator, and output the new learning discriminator and identification information to the respective terminal devices, the identification information being capable of identifying the image correct answer data used for learning of the new learning discriminator,
wherein the processor repeatedly performs a process of acquiring the plurality of learned discriminators obtained from the plurality of terminal devices, each of the plurality of learned discriminators being obtained by causing the learning discriminators output from the learning assistance device and provided in the plurality of respective terminal devices to perform learning using image correct answer data different from image correct answer data indicated by the output identification information in the respective terminal devices, and outputting the new learning discriminator and the identification information to the plurality of terminal devices.

2. The learning assistance device according to claim 1, wherein the identification information allowing each of the terminal devices to identify whether or not the image correct answer data learned by the learning discriminator to be output is image correct answer data learned by each of the terminal devices.

3. The learning assistance device according to claim 1, wherein the processor is further configured to output an actually operated discriminator that has learned the same image correct answer data as that of the new learning discriminator.

4. The learning assistance device according to claim 1, wherein the identification information of the image correct answer data is determined to be unique in all of the plurality of terminal devices, and
the processor is further configured to acquire identification information of the image correct answer data learned by each of the learned discriminators, and
output the identification information of the image correct answer data used for learning of the learning discriminator.

5. The learning assistance device according to claim 1, wherein the identification information of the image correct answer data includes terminal device identification information for identifying the plurality of terminal devices.

6. The learning assistance device according to claim 1, wherein the processor is further configured to distribute the identification information for identifying the image correct answer data to the plurality of terminal devices over a network.

7. The learning assistance device according to claim 1, wherein the processor is further configured to acquire the learned discriminator from the plurality of terminal devices over a network, and
output the new learning discriminator and the identification information of the image correct answer data used for learning of the learning discriminator to the plurality of terminal devices over the network.

8. The learning assistance device according to claim 7, wherein the processor is further configured to receive the identification information of the image correct answer data used for learning of each of the plurality of learned discriminators from each of the plurality of terminal devices over the network.

9. The learning assistance device according to claim 1, wherein the image correct answer data comprise a combination of medical image data and a correct answer data thereof.

10. A method of operating a learning assistance device including a processor, wherein the processor is configured to perform the steps of:
acquiring a plurality of learned discriminators obtained by causing learning discriminators provided in a plurality of respective terminal devices to perform learning using image correct answer data, from the respective terminal devices, each of the plurality of learned discriminators being learned at the respective terminal devices by using respective image correct answer data stored in the respective terminal devices;
obtaining a correct answer rate using an image set including a plurality of evaluation images for the plurality of learned discriminators, setting the learned discriminator having the highest correct answer rate among the plurality of learned discriminators as a new learning discriminator, and outputting the new learning discriminator and identification information to the respective terminal devices, the identification information being capable of identifying the image correct answer data used for learning of the new learning discriminator; and
repeatedly performing a process of acquiring the plurality of learned discriminators obtained from the plurality of terminal devices, each of the plurality of learned discriminators being obtained by causing the learning discriminators output from the learning assistance device and provided in the plurality of respective terminal devices to perform learning using image correct answer data different from image correct answer data indicated by the output identification information in the respective terminal devices, and outputting the new learning discriminator and the identification information to the plurality of terminal devices.

11. A non-transitory computer-readable recording medium storing therein a learning assistance program that causes a processor of a computer to:
acquire a plurality of learned discriminators obtained by causing learning discriminators provided in a plurality of respective terminal devices to perform learning using image correct answer data, from the respective terminal devices, each of the plurality of learned discriminators being learned at the respective terminal devices by using respective image correct answer data stored in the respective terminal devices; and obtain a correct answer rate using an image set including a plurality of evaluation images for the plurality of learned discriminators, set the learned discriminator having the highest correct answer rate among the plurality of learned discriminators as a new learning discriminator, and output the new learning discriminator and identification information to the respective terminal devices, the identification information being capable of identifying the image correct answer data used for learning of the new learning discriminator, wherein the processor repeatedly performs a process of acquiring the plurality of learned discriminators obtained from the plurality of terminal devices, each of the plurality of learned discriminators being obtained by causing the learning discriminators output from the learning assistance device and provided in the plurality of respective terminal devices to perform learning using image correct answer data different from image correct answer data indicated by the output identification information in the respective terminal devices, and outputting the new learning discriminator and the identification information to the plurality of terminal devices.

12. A learning assistance system in which a plurality of terminal devices and a learning assistance device are connected by a network, wherein the terminal device includes a first processor configured to output a learned discriminator obtained by causing a learning discriminator to perform learning using image correct answer data to the learning assistance device over a network, and the learning assistance device includes a second processor configured to acquire a plurality of learned discriminators from the plurality of respective terminal devices over the network, obtain a correct answer rate using an image set including a plurality of evaluation images for the plurality of learned discriminators, set the learned discriminator having the highest correct answer rate among the plurality of learned discriminators as a new learning discriminator, and output the new learning discriminator and identification information capable of identifying the image correct answer data used for learning of the new learning discriminator to the plurality of terminal devices over the network, wherein the first processer is further configured to acquire the learning discriminator output from the learning assistance device and identification information of image correct answer data used for learning of the acquired learning discriminator over the network, and output the learned discriminator obtained by causing the learning discriminator acquired from the learning assistance device to perform learning using image correct answer data different from the identification information used for learning of the learning discriminator acquired from the learning assistance device.

13. The learning assistance system according to claim 12, wherein the first processer is further configured to acquire an actually operated discriminator caused to learn the same image correct answer data as that of the learning discriminator output from the learning assistance device, and acquire a discrimination result of discriminating an image that is a discrimination target using the actually operated discriminator.

14. A terminal device comprising a processor configured to:

acquire a learning discriminator including image correct answer data, an actually operated discriminator having learned the same image correct answer data as that of the learning discriminator, and identification information capable of identifying the learned image correct answer data;

acquire a discrimination result of discriminating an image that is a discrimination target using the actually operated discriminator; and output a learned discriminator obtained by causing the learning discriminator to learn image correct answer data different from the acquired identification information.

15. The terminal device according to claim 14, wherein the processor is further configured to output the identification information of the different image correct answer data.

16. The terminal device according to claim 14, wherein the processor is further configured to acquire the learning discriminator, the actually operated discriminator, and the identification information from a learning assistance device over a network, and output the learned discriminator over the network.

* * * * *